US005691190A

United States Patent [19]

Girard et al.

[11] Patent Number: 5,691,190
[45] Date of Patent: Nov. 25, 1997

[54] PHAFFIA RHODOZYMA MUTANTS, PROCESS FOR PRODUCING β-CAROTENE AND USE OF β-CAROTENE RICH BIOMASS

[75] Inventors: Patrick Girard, Les Ulis; Catherine Eliane Jeannie Javelot, Maisons Alfort; Barbu Dinu Vladimir Vladescu, Paris, all of France

[73] Assignee: Pernod Ricard, Paris, France

[21] Appl. No.: 542,796

[22] Filed: Oct. 13, 1995

Related U.S. Application Data

[63] Continuation of Ser. No. 183,305, Jan. 19, 1994, abandoned.

[30] Foreign Application Priority Data

Jan. 19, 1993 [FR] France .................................. 93 00463

[51] Int. Cl.[6] .............................. C12N 1/16; C12N 1/14; C12P 23/00
[52] U.S. Cl. ...................... 435/255.1; 435/67; 435/173.1; 435/173.8; 435/256.8; 435/911
[58] Field of Search .................................. 435/255.1, 67, 435/173.1, 173.8, 256.8, 911

[56] References Cited

PUBLICATIONS

Applied and Environmental Microbiology, vol. 56, No. 9, Sep. 1990, pp. 2944–2945.
Database WPI, Section Ch, Week 8530, Derwent Publications Ltd.
Chemical Abstracts, vol. 72, No. 13, Mar. 30, 1970, abstract No. 65371c.
Applied and Environmental Microbiology, vol. 55, No. 1, Jan. 1989, pp. 116–124.

*Primary Examiner*—Herbert J. Lilling
*Attorney, Agent, or Firm*—Jacobson, Price, Holman & Stern, PLLC

[57] ABSTRACT

The subject of the present invention is *Phaffia rhodozyma* mutants blocked in the step of conversion of β-carotene in the pathway of biosynthesis of astaxanthin.

The present invention also relates to a process for producing β-carotene using these mutants, for purposes of use in the preparation of foodstuffs or cosmetic or pharmaceutical products.

8 Claims, 3 Drawing Sheets

PHAFFIA RHODOZYMA MUTANTS, PROCESS FOR PRODUCING β-CAROTENE AND USE OF β-CAROTENE RICH BIOMASS

This is a continuation of application Ser. No. 08/183,305, filed Jan. 19, 1994, abandoned.

The present invention relates to *Phaffia rhodozyma* mutants blocked in the pathway of carotenogenesis, to processes for obtaining β-carotene, to the use of biomass of these mutants and to the use of β-carotene.

Chiefly known as the most important of the provitamins A, β-carotene is currently the subject of detailed epidemiological and clinical studies which appear to attribute to it physiological roles other than those associated with vitamin A.

In effect, since the conversion of β-carotene to vitamin A in the intestinal wall is regulated by the vitamin A level itself in the blood, a portion of the dietary β-carotene remains in the provitamin state and exerts an antioxidant function which is probably responsible for protection against certain forms of cancer, atherosclerosis, rheumatoid arthritis, senile cataract and parkinsonism. A daily dose of 5.2 to 6.0 mg of β-carotene in the food has been recommended as an important factor in preventing these diseases.

As β-carotene is also a natural pigment capable of replacing some synthetic colorants, and is viewed very favourably by consumers, considerable effort is currently being directed towards the production of new foodstuffs containing β-carotene, these products belonging to the category of new-generation foods termed "functional" foods. Moreover, β-carotene would appear to be a very effective sun protection agent, resulting in some applications in the cosmetic products industry.

Although carotenoids in general and β-carotene in particular are widespread in the living world, only plants and some microorganisms possess the enzyme equipment needed for their biosynthesis from acetyl-CoA, via mevalonic acid.

Among microorganisms, some fungi and algae synthesize carotenes (including β-carotene), whereas bacteria essentially produce xanthophylls. The processes for producing β-carotene in a fermenter proposed hitherto employ the alga Dunaliella (Ben Amotz & Avron, 1980) and the phycomycetes *Phycomyces blakesleeanus* (Murillo-Araujo et al., 82) and *Blakeslea trispora* (Ninet and Renaut, 1979).

As regards yeasts, with one exception, these microorganisms do not form the subject of industrial processes for producing carotenoids. Torulene, synthesized by red yeasts belonging to the genera Rhodotorula and Rhodosporidium, is only of minor interest, while the other carotenoids identified in yeasts (including β-carotene) are present in such small amounts that it seems scarcely possible to envisage an industrial exploitation.

The sole example of a carotenoid produced industrially by the use of yeasts is afforded by astaxanthin, a pigment characteristic of the yeast *Phaffia rhodozyma*. After optimization of the production, astaxanthin or the yeast biomass is used as a supplement in the feeding of salmon, salmon trout, shell fish, laying hens, and the like (Patent WO 91/02,060).

Carotenoids other than β-carotene do not possess either the vitamin potential of β-carotene or its anti-oxidant protective effect. However, the large yield from the operation of the pathway of biosynthesis of astaxanthin in *Phaffia rhodozyma*, together with the fact that this species virtually has the character of a food, suggested we might turn the properties of this yeast to good account in a process for producing β-carotene.

A production of β-carotene by yeasts would hence be advantageous since, on the one hand the latter are easier to culture in bulk than other microorganisms such as fungi and plants, and on the other hand the biomass of yeast mutants producing β-carotene could be used as such in products such as, in particular, foodstuffs and dietary, cosmetic, parapharmaceutical or pharmaceutical products.

The present invention provides *Phaffia rhodozyma* mutants blocked in the pathway of carotenogenesis and which accumulate β-carotene.

The pathway of biosynthesis of astaxanthin in *Phaffia rhodozyma* has been partially elucidated and is presented in FIG. 1.

The mutants according to the invention are probably blocked in the step of conversion of β-carotene to echinenone, in particular by UV treatment. These mutants are incapable of producing astaxanthin.

The subject of the present invention is, in effect, a process for obtaining *Phaffia rhodozyma* mutants producing β-carotene according to the invention, characterized in that:

1) a wild-type strain of *Phaffia rhodozyma* in culture is treated with a physical or chemical mutagenic agent, and 2) the yellow-coloured clones obtained after the treatment of step 1) are selected.

As mentioned in an embodiment in step 1), the wild-type strain of *Phaffia rhodozyma* is treated with a mutagenic agent consisting of ultraviolet rays.

The subject of the present invention is also a process for producing β-carotene, by fermentation of a mutant strain of *Phaffia rhodozyma* yeast according to the invention.

An increase is obtained in the production yield of β-carotene when the culture medium is enriched in mevalonic acid (mevalonic acid (MVA) is, in effect, a precursor of β-carotene in the pathway of biosynthesis of astaxanthin).

The present invention also provides crude preparations of β-carotene bereft of viable cells, obtained from the biomass of *Phaffia rhodozyma* mutants according to the invention.

The subject of the present invention is also the use of β-carotene obtained by a process according to the invention, for the preparation of foodstuffs or dietary, cosmetic, parapharmaceutical or pharmaceutical products.

The subject of the present invention is also the use of biomass, where appropriate dehydrated, of a mutant of *Phaffia rhodozyma* yeast according to the invention, as a β-carotene supplement in the preparation of foodstuffs or dietary, cosmetic, parapharmaceutical or pharmaceutical products.

The present invention provides, in addition, a process for producing β-ionone, by heating cells of a mutant of *Phaffia rhodozyma* yeast according to the invention.

Lastly, the subject of the present invention is the use of the biomass of a *Phaffia rhodozyma* yeast according to the invention as a source of β-ionone, in particular in the preparation of foodstuffs or dietary, cosmetic, parapharmaceutical or pharmaceutical products.

Further features and advantages of the present invention will become apparent in the light of the examples which follow.

EXAMPLE 1

Production of mutants

Cells of the wild-type strain CBS 6938 of *Phaffia rhodozyma* are cultured on a liquid medium (YPG) containing 1% of yeast extract, 1% of Bactopeptone and 2% of glucose, with stirring (150 rpm) at 25° C. 72-hour-old cultures are centrifuged for 5 min at 3000 g, and the cells are washed twice with distilled water and treated with UV for 50 sec at a distance of 35 cm from a germicidal lamp, corresponding to a dose of 1789 $jxs^{-1}xcm^2$. The survival rate is approximately 10%. The treated cells are plated out on dishes of solid YPG and incubated at 25° C. for 72 hours. Of $5 \times 10^4$ colonies examined, a few white colonies were identified, as well as two yellow-coloured colonies (PG 104 and PG 126) contrasting with the red colour of the wild-type colonies. The mutant PG 104 formed the subject of the subsequent experiments. Phaffia Rhodozyma PG 104 strain has been deposited under Deposit No. CBS 664–95 at Centraalbureau Voor Schimmelcultures (CBS), Netherlands, which is an International Depository Authority in accordance with the Budapest Treaty.

EXAMPLE 2

Identification of the carotenoids of the mutant PG 104

Figure 1:
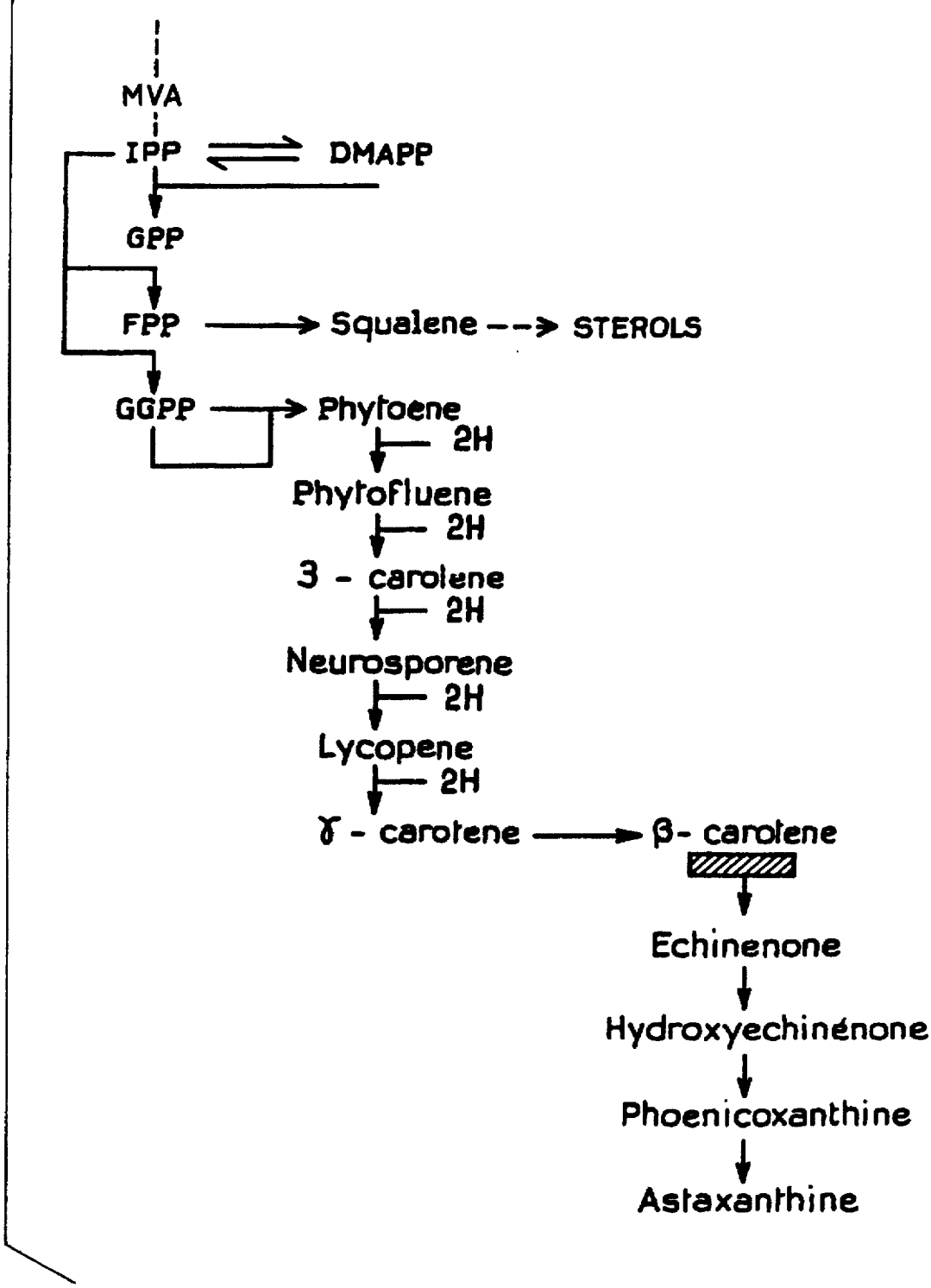
FIG. 1 shows the pathway MVA=mevalonic acid, IPP=isopentenyl pyrophosphate, DMAPP=dimethylallyl pyrophosphate, GPP=geranyl pyrophosphate, FPP=farnesyl pyrophosphate, GGPP=geranyl pyrophosphate; the shaded bar indicates the probable site of the mutation of biosynthesis of astaxanthin in *Phaffia rhodozyma*.
Figure 2A:
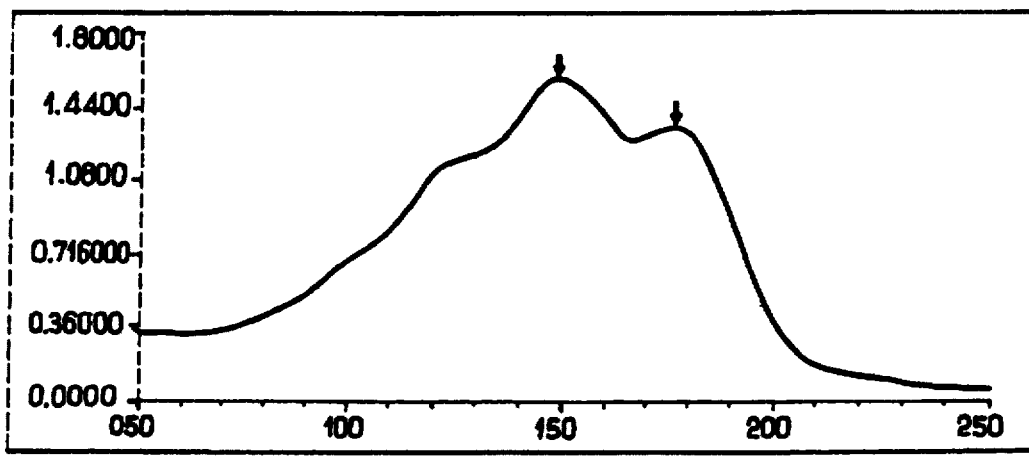
FIG. 2A shows the absorption spectrum of the extract of the strain PG 104.
Figure 2B:
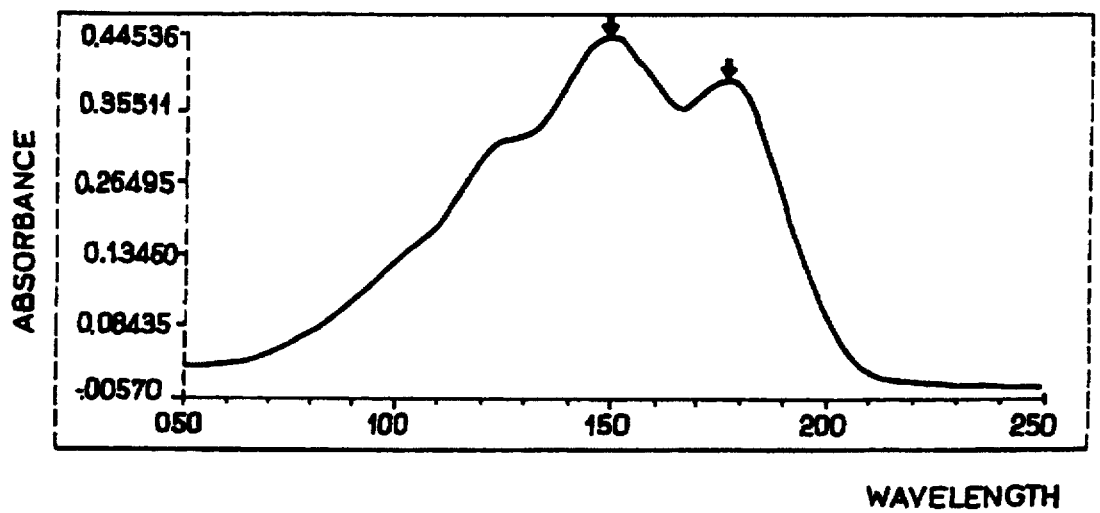
FIG. 2B shows the absorption spectrum of the reference product (pure beta-carotene, Sigma)

100 ml of SD medium (50.67% of Bacto-yeast nitrogen base without amino acids and 2% of glucose) are placed in 1000-ml Erlenmeyer flasks and inoculated with $10^6$ cells/ml of the strain PG 104 taken from a preculture in YPG. The cultures are incubated at 25° C. with stirring (150 rpm) and, after 72 hours, the cells are harvested by centrifugation and subjected to a lytic treatment: to 200 ml of cell suspension in 0.1M citrate-phosphate buffer, pH 5.6, containing $10^7$ cpm, 6 mg/ml of enzyme preparation (Novozym 234) are added; after incubation for 60 min at 25° C. with gentle stirring, microscopic examination shows a virtually 100% lysis of the cell walls. The protoplast preparation is then treated with acetone and the carotenoids are extracted with petroleum ether. The UV-VIS spectrum of the extract (FIG. 2) is identical to that of the reference product (pure β-carotene, Sigma).

Figure 3A:
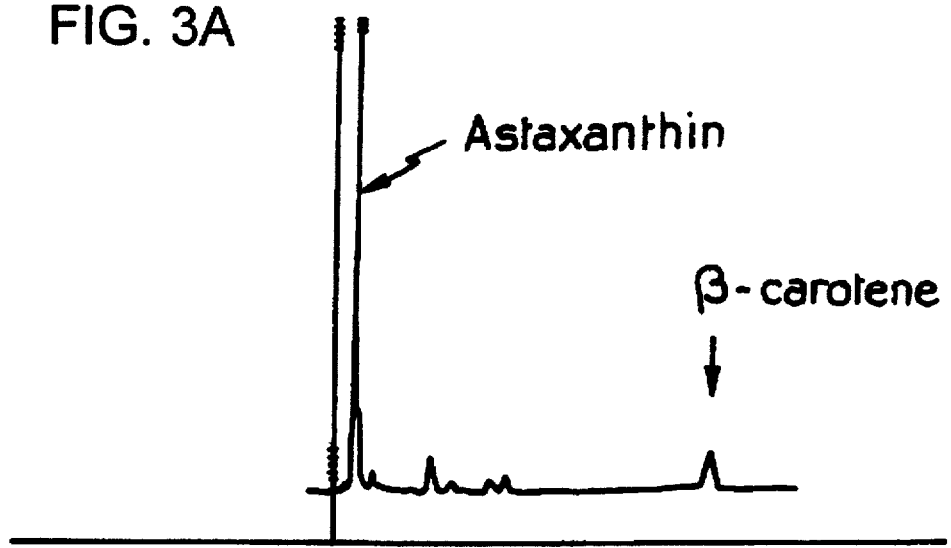
FIG. 3A shows the HPLC analysis of the extracts of the wild-type strain CBS 6938 of *Phaffia rhodozyma*.
Figure 3B:
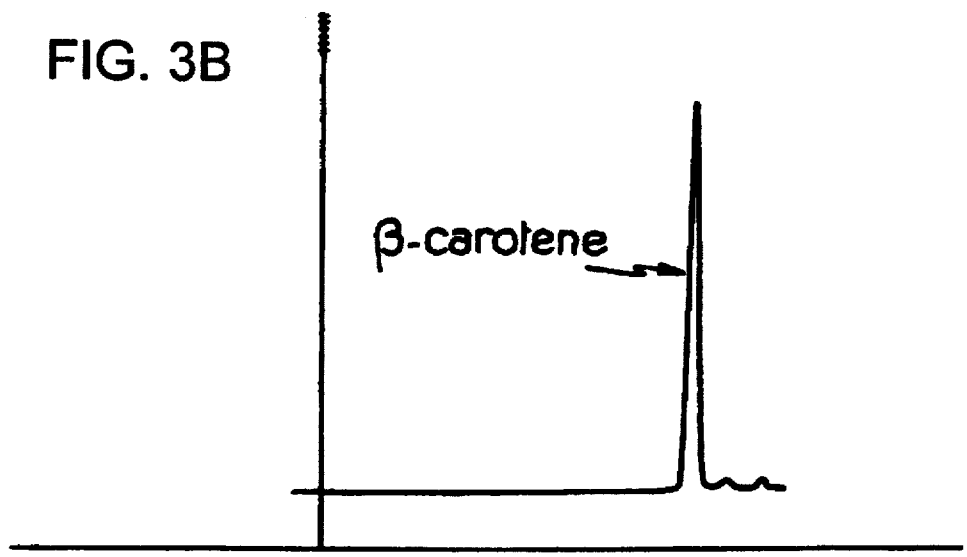
FIG. 3B shows the HPLC analysis of the extracts of the wild-type strain CBS 6938 of the mutant PG 104.
Figure 3C:
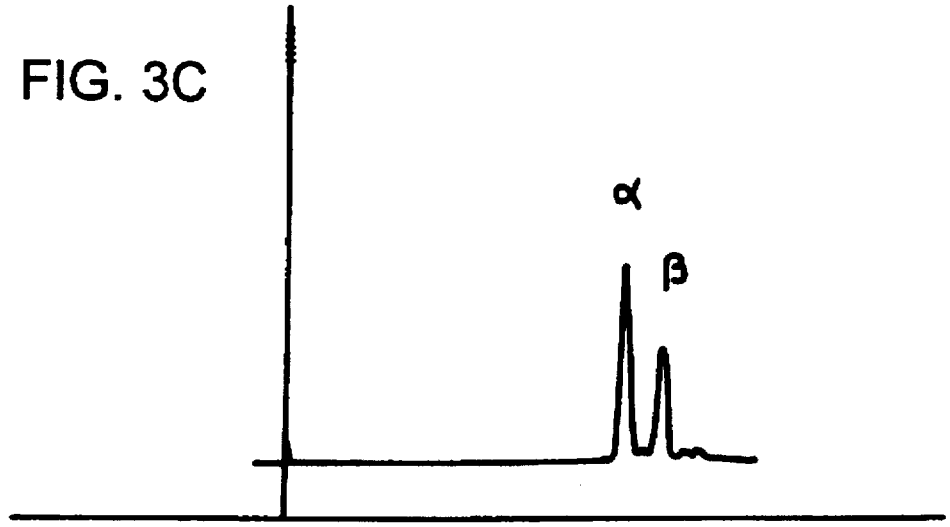
FIG. 3C shows the HPLC analysis of the extracts of the wild-type strain CBS 6938 of the reference products alpha-carotene, Sigma, and beta-carotene, Sigma.

HPLC analysis (FIG. 3) on a Microbondapak RP 18 column (Waters) with methanol as mobile phase shows the presence of a single peak corresponding to that of pure β-carotene in the case of the mutant PG 104, in contrast to the wild-type strain which contains astaxanthin as the major peak, but also small amounts of other probable intermediates of the carotenoid pathway.

A comparison with the relative proportions of different carotenoids in a wild-type strain (Table 1) shows clearly that the mutant PG 104 produces β-carotene almost exclusively. It probably corresponds to a mutational block in the step of conversion of β-carotene to echinenone.

TABLE 1

| CAROTENOIDS OF PHAFFIA RHODOZYMA (% OF TOTAL CAROTENOIDS) | | |
|---|---|---|
| | WILD-TYPE * | MUTANT (P-104) |
| Neurosporene | 0.01 | 0 |
| Lycopene | 0.01 | ? |
| γ-Carotene | 0.01 | 0 |
| β-Carotene | 2–2.5 | 92 |
| Echinenone | 2–4 | 0 |
| Hydroxyechinenone | 3–4 | 0 |
| Phoenicoxanthin | 5–7 | 0 |
| Astaxanthin | 83–87 | 0 |

* From Andrewes et al. (1976)

EXAMPLE 3

Production of β-carotene with the mutant PG 104

Different culture media and conditions, as well as the effect of certain supplements on the biosynthesis of β-carotene by PG 104, were tested in order to establish the parameters enabling this production to be increased. The results are presented in Table 2.

Following these tests, the following culture parameters were chosen for an optimum production of β-carotene:
Culture medium: SGly-CH-MVA
Inoculum: $10^6$ cpm
Volume: 1/10 of the volume of the flask
Temperature: 25° C.
Stirring: 150 rpm Under these conditions, up to 10 mg of β-carotene per liter of culture are obtained after 96 hours.

TABLE 2

| PRODUCTION OF β-CAROTENE IN DIFFERENT CULTURE MEDIA | | |
|---|---|---|
| | β-CAROTENE | |
| Medium | mg/l | mg/g dry weight |
| YPG | 0.37 | 0.07 |
| YPGly | 2.35 | 0.32 |
| SD | 1.80 | 0.50 |
| SGly | 0.05 | 0.12 |
| PDB | 2.30 | 0.29 |
| MG | 2.70 | 0.39 |
| MGly | 0.46 | 0.31 |
| SD-MVA | 4.70 | 1.12 |
| SGly-CH | 7.90 | 0.87 |
| SGly-CH-MVA | 9.95 | 1.08 |

YPG=1% Yeast extract, 1% Bactopeptone, 2% Glucose
YPGly 32 1% Yeast extract, 1% Bactopeptone, 3% v/v Glycerol
SD=0.67% Bacto-yeast nitrogen base, 2% Glucose
SGly=0.67% Bacto-yeast nitrogen base, 3% v/v Glycerol
PDB=2.4% Potato dextrose (Difco)
MG=2% Meat extract, 2% Glucose
MGly=2% Meat extract, 3% (v/v) Glycerol
SD-MVA=SD+500 mg/l mevalonic acid
SGly-CH=SGly+5 g/l casein hydrolysate
SGly-CH-MVA=SGly+5 g/l casein hydrolysate+500 mg/l mevalonic acid

EXAMPLE 4

Crude preparation of β-carotene from cells of the mutant PG 104 of *Phaffia rhodozyma*

PG 104 cells cultured under the standard conditions are harvested by centrifugation and washed once with distilled water. To 1 g (wet weight) of cells, 100 ml of absolute ethanol are added and the suspension is stirred for 1 hour at 150 rpm. The cells are harvested by centrifugation, and the pellet is distributed in layers 1–2 mm thick on Petri dishes and dried for 24 hours at room temperature. A powder containing 2 mg of β-carotene per gram is obtained. Aliquots of this powder are plated out on dishes of solid YPG, and the absence of growth after 2 weeks shows that the preparation does not contain any living cell.

This preparation may be used as a β-carotene supplement in fruit juices and any other foodstuff, as well as in cosmetic products and in animal feeds.

EXAMPLE 5

β-Carotene-rich preparation from Phaffia rhodozyma PG 104 cells

Cells harvested in 100 ml of culture are treated with Novozym (as described in Example 2) and extracted 5 times with acetone. The extracts are combined and the cell debris is removed by centrifugation. The acetone supernatant is placed in a separating funnel; 10 ml of petroleum ether and 1 ml of saturated NaCl are added. The strongly coloured upper phase (petroleum ether) is recovered; the acetone phase is extracted a second time with petroleum ether, and the ether extracts are combined, filtered, dried over anhydrous $Na_2SO_4$ and taken up in 1 ml of petroleum ether. The identity of the carotenoid extracted is confirmed by spectrophotometry. The final extract contains 1 g of β-carotene per liter.

EXAMPLE 6

Production of β-ionone during the preparation of distilled beverages

β-Ionone is an expensive flavouring used in the food industry. Distillery malt wort (initial density 1060) is fermented with a traditional distillery strain to a density of 997. Before the distillation, 1 g of *Phaffia rhodozyma* PG 104 cells previously treated with Novozym is added. In the low wine obtained after distillation, the presence of traces of β-ionone are demonstrated by GC-MS, these being absent in the control product.

BIBLIOGRAPHY

Ben-Amotz A., Avron M. (1983) On factors which determine massive β-carotene accumulation in the halotolerant alga *Dunaliella bardawil*. Plant Physiol. 72: 593–597.

Murillo-Araujo F. J., Calderon I. L., Lopez-Diaz L., Cerda-Olmedo E. (1978) Carotene superproducing strains of Phycomyces. Appl. Environ. Microbiol. 36: 639–642.

Ninet L., Renaut J. (1979) In "Microbial Technology", H. J. Peppler & D. Perlman eds., 2nd Ed. Vol. 1, pp. 529–544, Academic Press, New York.

Igene Biotechnology, Inc. (1989) Processes for in vivo production of astaxanthin and *Phaffia rhodozyma* yeast of enhanced astaxanthin content. Patent WO 91/02,060.

Andrews A. G., Phaff H. J., Starr M. P. (1976) Carotenoids of *Phaffia rhodozyma*, a red-pigmented fermenting yeast. Phytochemistry 15: 1003–1007.

We claim:

1. *Phaffia rhodozyma* mutant blocked in the step of conversion of β-carotene in the pathway of biosynthesis of astaxanthin characterized by being obtained by a process comprising the steps of:

(1) treating with a physical or chemical mutagenic agent of a wild type *Phaffia rhodozyma* CBS 6938 strain in culture; and (2) selecting the yellow-colored clones obtained after step 1.

2. Process for obtaining *Phaffia rhodozyma* mutants producing β-carotene according to claim 1, characterized in that:

1) a wild-type strain of *Phaffia rhodozyma* in culture is treated with a physical or chemical mutagenic agent, and 2) the yellow-coloured clones obtained after the treatment of step 1) are selected.

3. Process according to claim 2, characterized in that, in step 1), the wild-type strain of *Phaffia rhodozyma* is treated with a mutagenic agent consisting of ultraviolet rays.

4. A culture containing the microorganism *Phaffia rhodozyma* mutant according to claim 1, further comprising mevalonic acid (MVA).

5. A culture containing the microorganism *Phaffia rhodozyma* mutant, according to claim 1, said culture being capable of producing β-ionone upon heating the cells of the mutant *Phaffia rhodozyma*.

6. *Phaffia rhodozyma* mutant according to claim 1 selected from a group consisting of PG 104 (CBS 664-95).

7. The mutant of claim 1 wherein, in step 1, the wild-type strain of *Phaffia rhodozyma* is treated with a mutagenic agent consisting of ultraviolet rays at a dose higher than the natural dose.

8. *Phaffia rhodozyma* mutant of claim 1, wherein said mutant contains no astaxanthin and 92% β-carotene.

* * * * *